United States Patent
Mikkelsen et al.

(10) Patent No.: US 9,085,750 B2
(45) Date of Patent: *Jul. 21, 2015

(54) STABILIZED SUBTILISIN COMPOSITION

(75) Inventors: Lise Munch Mikkelsen, Roedovre (DK); Francesco Ponzini, Corsico (IT); Roberto Bisaccia, Monte Giovanni (IT); Renato Canevotti, Concorezzo (IT)

(73) Assignee: Novozymes A/S, Bagsvaerd (DK)

( * ) Notice: Subject to any disclaimer, the term of this patent is extended or adjusted under 35 U.S.C. 154(b) by 16 days.

This patent is subject to a terminal disclaimer.

(21) Appl. No.: 14/129,748

(22) PCT Filed: Jun. 29, 2012

(86) PCT No.: PCT/EP2012/062760
§ 371 (c)(1),
(2), (4) Date: May 27, 2014

(87) PCT Pub. No.: WO2013/004636
PCT Pub. Date: Jan. 10, 2013

(65) Prior Publication Data
US 2014/0336098 A1   Nov. 13, 2014

Related U.S. Application Data

(60) Provisional application No. 61/503,762, filed on Jul. 1, 2011.

(30) Foreign Application Priority Data

Jul. 1, 2011   (EP) ..................................... 11172357

(51) Int. Cl.
| C07K 5/08 | (2006.01) |
|---|---|
| C11D 3/386 | (2006.01) |
| C07K 5/062 | (2006.01) |
| C07K 5/072 | (2006.01) |
| C07K 5/083 | (2006.01) |
| C07K 5/087 | (2006.01) |
| C07K 5/065 | (2006.01) |

(52) U.S. Cl.
CPC ........ *C11D 3/38663* (2013.01); *C07K 5/06026* (2013.01); *C07K 5/06043* (2013.01); *C07K 5/06052* (2013.01); *C07K 5/06078* (2013.01); *C07K 5/06095* (2013.01); *C07K 5/0808* (2013.01); *C07K 5/0812* (2013.01); *C11D 3/38618* (2013.01)

(58) Field of Classification Search
None
See application file for complete search history.

(56) References Cited

U.S. PATENT DOCUMENTS

| 4,478,745 A | 10/1984 | Bajusz et al. |
|---|---|---|
| 4,691,007 A | 9/1987 | Dutta et al. |
| 4,703,036 A | 10/1987 | Bajusz et al. |
| 5,436,229 A * | 7/1995 | Ruterbories et al. ......... 514/14.9 |
| 5,578,574 A | 11/1996 | Shuman et al. |
| 6,500,802 B1 | 12/2002 | Tao et al. |

FOREIGN PATENT DOCUMENTS

| WO | 94/04651 A1 | 3/1994 | |
|---|---|---|---|
| WO | 95/02579 A1 | 1/1995 | |
| WO | WO 98/13458 * | 2/1998 | ............. C11D 3/386 |
| WO | 98/13458 A1 | 4/1998 | |
| WO | 98/13459 A1 | 4/1998 | |
| WO | 98/13460 A1 | 4/1998 | |
| WO | 98/47523 A1 | 10/1998 | |
| WO | 2009/118375 A2 | 10/2009 | |
| WO | 2011/036153 A1 | 3/2011 | |

* cited by examiner

*Primary Examiner* — Karlheinz R Skowronek
*Assistant Examiner* — Mindy Newman
(74) *Attorney, Agent, or Firm* — Kelly Reynolds

(57) ABSTRACT

The conversion of a peptide aldehyde to a hydrosulfite adduct can be used to increase the aqueous solubility in the purification of the peptide aldehydes. Advantageously, this hydrosulfite adduct is itself effective as a subtilisin inhibitor and stabilizer and it can also stabilize a second enzyme if present. The hydrosulfite adduct is effective as a subtilisin inhibitor, and it maintains its inhibitory and stabilizing effect in a liquid detergent during storage. Thus, use of the hydrosulfite adduct can avoid the cost and time of converting it back to the peptide aldehyde and subsequent drying of the peptide aldehyde can be saved, and this can avoid the inconvenience of handling the peptide aldehyde in powder form or as a highly diluted aqueous solution.

21 Claims, No Drawings

SEQUENCE LISTING

```
<160> NUMBER OF SEQ ID NOS: 9

<210> SEQ ID NO 1
<211> LENGTH: 4
<212> TYPE: PRT
<213> ORGANISM: Artificial Sequence
<220> FEATURE:
<223> OTHER INFORMATION: Peptide aldehyde

<400> SEQUENCE: 1

Leu Gly Ala Tyr
1

<210> SEQ ID NO 2
<211> LENGTH: 4
<212> TYPE: PRT
<213> ORGANISM: Artificial Sequence
<220> FEATURE:
```

```
<223> OTHER INFORMATION: Peptide aldehyde

<400> SEQUENCE: 2

Phe Gly Ala Tyr
1

<210> SEQ ID NO 3
<211> LENGTH: 4
<212> TYPE: PRT
<213> ORGANISM: Artificial Sequence
<220> FEATURE:
<223> OTHER INFORMATION: Peptide aldehyde

<400> SEQUENCE: 3

Tyr Gly Ala Tyr
1

<210> SEQ ID NO 4
<211> LENGTH: 4
<212> TYPE: PRT
<213> ORGANISM: Artificial Sequence
<220> FEATURE:
<223> OTHER INFORMATION: Peptide aldehyde

<400> SEQUENCE: 4

Phe Gly Ala Leu
1

<210> SEQ ID NO 5
<211> LENGTH: 4
<212> TYPE: PRT
<213> ORGANISM: Artificial Sequence
<220> FEATURE:
<223> OTHER INFORMATION: Peptide aldehyde

<400> SEQUENCE: 5

Phe Gly Ala Phe
1

<210> SEQ ID NO 6
<211> LENGTH: 4
<212> TYPE: PRT
<213> ORGANISM: Artificial Sequence
<220> FEATURE:
<223> OTHER INFORMATION: Peptide aldehyde

<400> SEQUENCE: 6

Phe Gly Val Tyr
1

<210> SEQ ID NO 7
<211> LENGTH: 4
<212> TYPE: PRT
<213> ORGANISM: Artificial Sequence
<220> FEATURE:
<223> OTHER INFORMATION: Peptide aldehyde

<400> SEQUENCE: 7

Phe Gly Ala Met
1

<210> SEQ ID NO 8
<211> LENGTH: 4
<212> TYPE: PRT
<213> ORGANISM: Artificial Sequence
<220> FEATURE:
<223> OTHER INFORMATION: Peptide aldehyde
```

```
<400> SEQUENCE: 8

Trp Leu Val Tyr
1

<210> SEQ ID NO 9
<211> LENGTH: 4
<212> TYPE: PRT
<213> ORGANISM: Artificial Sequence
<220> FEATURE:
<223> OTHER INFORMATION: Peptide aldehyde

<400> SEQUENCE: 9

Leu Gly Ala Leu
1
```

STABILIZED SUBTILISIN COMPOSITION

CROSS-REFERENCE TO RELATED APPLICATIONS

This application is a 35 U.S.C. 371 national application of PCT/EP2012/062760 filed Jun. 29, 2012, which claims priority or the benefit under 35 U.S.C. 119 of European application no. 11172357.3 filed Jul. 1, 2011 and U.S. provisional application No. 61/503,762 filed Jul. 1, 2011, the contents of which are fully incorporated herein by reference.

REFERENCE TO A SEQUENCE LISTING

This application contains a Sequence Listing in computer readable form.

TECHNICAL FIELD

The present invention relates to a composition comprising a subtilisin which is stabilized by a peptide aldehyde derivative. It also relates to a method of preparing the composition, and to a compound for use in the composition.

BACKGROUND OF THE INVENTION

WO 98/13458, WO 94/04651, WO 98/13460, WO 95/25791, and WO 2009/118375 disclose liquid detergents with a subtilisin-type protease stabilized by a peptide aldehyde. WO 2011/036153 discloses that the addition of a peptide aldehyde to a particulate subtilisin-containing detergent can improve the detergency.

It is well known that aldehydes can form soluble adducts with $NaHSO_3$ (bisulfite or hydrosulfite adducts) and that peptide aldehydes tend to be sparingly water soluble.

WO 98/47523 and U.S. Pat. No. 6,500,802 disclose peptidyl-2-amino-1-hydroxyalkanesulfonic acids and their use as protease inhibitors. U.S. Pat. No. 5,436,229 discloses bisulfite adducts of L-Arginine aldehyde derivatives and their use as thrombin inhibitors.

U.S. Pat. Nos. 4,703,036, 4,478,745 and 5,578,574 disclose methods of preparing peptide aldehydes in dry form.

SUMMARY OF THE INVENTION

In the large-scale production of stabilized subtilisin compositions, it is strongly preferred to handle liquid raw materials, both for safety and process considerations. Peptide aldehydes tend to be sparingly water soluble which makes the preparation of concentrated aqueous solutions difficult or impossible and necessitates the use of either dry product or highly dilute aqueous solutions when making stabilized subtilisin solutions for use in liquid formulations or for granulation to make granular compositions.

The conversion of the peptide aldehyde to a hydrosulfite adduct can be used to increase the aqueous solubility in the purification of the peptide aldehydes. Advantageously, we have found that this hydrosulfite adduct is itself effective as a subtilisin inhibitor and stabilizer and that it can also stabilize a second (non-subtilisin) enzyme if present. We have found the hydrosulfite adduct to be effective as subtilisin inhibitor, and we have found that it maintains its inhibitory and stabilizing effect in a liquid detergent during storage. Thus, use of the hydrosulfite adduct can avoid the cost and time of converting it back to the peptide aldehyde and subsequent drying of the peptide aldehyde can be saved, and this can avoid the inconvenience of handling the peptide aldehyde in powder form or as highly diluted aqueous solution. Furthermore, the addition of a peptide aldehyde bisulfite adduct may also improve the detergency (wash performance) of a subtilisin-containing detergent.

Accordingly, the invention provides a composition comprising a subtilisin and a peptide aldehyde hydrosulfite adduct, having the formula $X-B^1-NH-CHR-CHOH-SO_3M$. The groups in the formula have the following meaning:

a) M is H (hydrogen) or an alkali metal, preferably Na or K;
b) R is a group such that NH—CHR—CO is an L or D-amino acid residue (in the following denoted $B^0$);
c) $B^1$ is one amino acid residue; and
d) X consists of one or more amino acid residues (preferably one or two), optionally comprising an N-terminal protection group.

The invention further provides a method of preparing the composition, which method comprises mixing a subtilisin, an aqueous solution comprising a peptide aldehyde hydrosulfite adduct having the formula $X-B^1-NH-CHR-CHOH-SO_3M$ (wherein M, R, $B^1$ and X are defined as above), and optionally a surfactant.

Additionally, the invention provides a compound for use in the composition, which compound is a peptide aldehyde hydrosulfite adduct having the formula $X-B^1-NH-CHR-CHOH-SO_3M$. R may be p-hydroxy-benzyl, and M, $B^1$ and X are defined as above

DETAILED DESCRIPTION OF THE INVENTION

Stabilized Subtilisin Composition

The composition of the invention comprises a subtilisin and a peptide aldehyde hydrosulfite adduct, and it may optionally comprise a second enzyme. The composition may be in liquid or granular form. It may be a detergent composition which further comprises a surfactant.

In a composition such as a liquid or granular detergent, the amount of each enzyme (subtilisin and optional second enzyme) will typically be 0.04-80 micro-M (or micro-mole/kg), in particular 0.2-30 micro-M, especially 0.4-20 micro-M (generally 1-2000 mg/l or mg/kg, in particular 5-750 mg/l, especially 10-500 mg/l) calculated as pure enzyme protein. In a composition such as an enzyme concentrate the amount of each enzyme will typically be 0.01-20 mM, in particular 0.04-10 mM, especially 0.1-5 mM (generally 0.3-500 g/l, in particular 1-300 g/l, especially 3-150 g/l) calculated as pure enzyme protein.

The molar ratio of enzyme stabilizer or inhibitor according to the invention to subtilisin is at least 1:1 or 1.5:1, and it is less than 1000:1, more preferred less than 500:1, even more preferred from 100:1 to 2:1 or from 20:1 to 2:1, or most preferred, the molar ratio is from 10:1 to 3:1.

Peptide Aldehyde

The bisulfite adduct used in the method can be derived from a peptide aldehyde with the formula $X-B^1-B^0-H$ wherein the groups are defined as above with $B^0$ being a single amino acid residue with L- or D-configuration with the formula: NH—CHR—CO.

NH—CHR—CO ($B^0$) is an L or D-amino acid residue, where R may be an aliphatic or aromatic side chain, e.g., aralkyl such as benzyl, where R may be optionally substituted. More particularly, the $B^0$ residue may be bulky, neutral, polar, hydrophobic and/or aromatic, optionally substituted. Examples are the D- or L-form of Tyr (p-tyrosine), m-tyrosine, 3,4-dihydroxyphenylalanine, Phe, Val, Met, norvaline (Nva), Leu, Ile or norleucine (Nle); particularly Tyr, m-tyrosine, 3,4-dihydroxyphenylalanine, Phe, Val, Met, Nva or Nle.

In the above formula, X—B$^1$—B$^0$—H, the B$^1$ residue may particularly be small, aliphatic, hydrophobic and/or neutral. Examples are alanine (Ala), cysteine (Cys), glycine (Gly), proline (Pro), serine (Ser), threonine (Thr), valine (Val), norvaline (Nva) and norleucine (Nle); particularly Ala, Cys, Gly, Ser, Thr, Val, Nva and Nle.

X may in particular be one or two amino acid residues with an optional N-terminal protection group (i.e. the compound is a tri- or tetrapeptide aldehyde with or without a protection group). Thus, X may be B$^2$, B$^3$—B$^2$, Z—B$^2$, Z—B$^3$—B$^2$ where B$^3$ and B$^2$ each represents one amino acid residue, and Z is an N-terminal protection group.

The B$^2$ residue may in particular be small, aliphatic and/or neutral, e.g., Ala, Gly, Thr, Arg, Leu, Phe or Val; particularly Gly, Thr or Val.

The B$^3$ residue may in particular be bulky, hydrophobic, neutral and/or aromatic, optionally substituted, e.g., Phe, Tyr, Trp, Phenylglycine, Leu, Val, Nva, Nle or Ile.

The N-terminal protection group Z (if present) may be selected from formyl, acetyl (Ac), benzoyl, trifluoroacetyl, fluoromethoxy carbonyl, methoxysuccinyl, aromatic and aliphatic urethane protecting groups, benzyloxycarbonyl Cbz), t-butyloxycarbonyl, adamantyloxycarbonyl, p-methoxybenzyl carbonyl (MOZ), benzyl (Bn), p-methoxybenzyl (PMB) or p-methoxyphenyl (PMP), methoxycarbonyl (Moc); methoxyacetyl (Mac); methyl carbamate or a methylamino carbonyl/methyl urea group. In the case of a tetrapeptide aldehyde with a protection group (i.e. X=Z—B$^3$—B$^2$), Z is preferably a small aliphatic group, e.g., formyl, acetyl, fluoromethoxy carbonyl, t-butyloxycarbonyl, methoxycarbonyl (Moc); methoxyacetyl (Mac); methyl carbamate or a Methylamino carbonyl/methyl urea group. In the case of a tripeptide aldehyde with a protection group (i.e. X=Z—B$^2$), Z is preferably a bulky aromatic group such as benzoyl, benzyloxycarbonyl, p-methoxybenzyl carbonyl (MOZ), benzyl (Bn), p-methoxybenzyl (PMB) or p-methoxyphenyl (PMP).

Suitable peptide aldehydes are described in WO 94/04651, WO 95/25791, WO 98/13458, WO 98/13459, WO 98/13460, WO 98/13461, WO 98/13461, WO 98/13462, WO 2007/141736, WO 2007/145963, WO 2009/118375, WO 2010/055052 and WO 2011/036153. More particularly, the peptide aldehyde may be Z-RAY-H, Ac-GAY-H, Z-GAY-H, Z-GAL-H, Z-VAL-H, Z-GAF-H, Z-GAV-H, Z-GGY-H, Z-GGF-H, Z-RVY-H, Z-LVY-H, Ac-LGAY-H, Ac-FGAY-H, Ac-YGAY-H, Ac-FGAL-H, Ac-FGAF-H, Ac-FGVY-H, Ac-FGAM-H, Ac-WLVY-H, MeO-CO-VAL-H, MeNCO-VAL-H, MeO-CO-FGAL-H, MeO-CO-FGAF-H, MeSO2-FGAL-H, MeSO2-VAL-H, PhCH2O(OH)(O)P-VAL-H, EtSO2-FGAL-H, PhCH2SO2-VAL-H, PhCH2O(OH)(O)P-LAL-H, PhCH2O(OH)(O)P-FAL-H, or MeO(OH)(O)P-LGAL-H. Here, Z is benzyloxycarbonyl, Me is methyl, Et is ethyl, Ac is acetyl, H is hydrogen, and the other letters represent amino acid residues denoted by standard single letter notification (e.g., F=Phe, Y=Tyr, L=Leu). Alternatively, the peptide aldehyde may have the formula as described in WO 2010/055052:

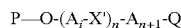

wherein Q is hydrogen, CH$_3$, CX$_3$, CHX$_2$, or CH$_2$X, wherein X is a halogen atom;

wherein one X' is the "double N-capping group" CO, CO—CO, CS, CS—CS or CS—CO, most preferred urido (CO), and the other X' es are nothing, wherein n=1-10, preferably 2-5, most preferably 2, wherein each of A$_i$ and A$_{n+1}$ is an amino acid residue having the structure:

—NH—CR—CO— for a residue to the right of X=—CO—, or

—CO—CR—NH— for a residue to the left of X=—CO— wherein R is H— or an optionally substituted alkyl or alkylaryl group which may optionally include a hetero atom and may optionally be linked to the N atom, and wherein P is hydrogen or any C-terminal protection group. Examples of such peptide aldehydes include α-MAPI, β-MAPI, F-urea-RVY-H, F-urea-GGY-H, F-urea-GAF-H, F-urea-GAY-H, F-urea-GAL-H, F-urea-GA-Nva-H, F-urea-GA-Nle-H, Y-urea-RVY-H, Y-urea-GAY-H, F—CS-RVF-H, F—CS-RVY-H, F—CS-GAY-H, Antipain, GE20372A, GE20372B, Chymostatin A, Chymostatin B, and Chymostatin C.

Further examples of peptide aldehydes are disclosed in WO 2010/055052 and WO 2009/118375, WO 94/04651, WO 98/13459, WO 98/13461, WO 98/13462, WO 2007/145963, (P&G) hereby incorporated by reference.

Peptide Aldehyde Hydrosulfite Adduct

The peptide aldehyde hydrosulfite adduct may be derived from the peptide aldehydes described above.

Particular examples are Cbz-RA-NHCH(CH$_2$C$_6$H$_4$OH)C(OH)(SO$_3$M)-H, Ac-GA-NHCH(CH$_2$C$_6$H$_4$OH)C(OH)(SO$_3$M)-H, Cbz-GA-NHCH(CH$_2$C$_6$H$_4$OH)C(OH)(SO$_3$M)-H, Cbz-GA-NHCH(CH$_2$CH(CH$_3$)$_2$))C(OH)(SO$_3$M)-H, Cbz-VA-NHCH(CH$_2$CH(CH$_3$)$_2$))C(OH)(SO$_3$M)-H, Cbz-GA-NHCH(CH$_2$Ph)C(OH)(SO$_3$M)-H, Cbz-GA-NHCH(CH(CH$_3$)$_2$)C(OH)(SO$_3$M)-H, Cbz-GG-NHCH(CH$_2$C$_6$H$_4$OH)C(OH)(SO$_3$M)-H, Cbz-GG-NHCH(CH$_2$Ph)C(OH)(SO$_3$M)-H, Cbz-RV-NHCH(CH$_2$C$_6$H$_4$OH)C(OH)(SO$_3$M)-H, Cbz-LV-NHCH(CH$_2$C$_6$H$_4$OH)C(OH)(SO$_3$M)-H, Ac-LGA-NHCH(CH$_2$C$_6$H$_4$OH)C(OH)(SO$_3$M)-H, Ac-FGA-NHCH(CH$_2$C$_6$H$_4$OH)C(OH)(SO$_3$M)-H, Ac-YGA-NHCH(CH$_2$C$_6$H$_4$OH)C(OH)(SO$_3$M)-H, Ac-FGA-NHCH(CH$_2$CH(CH$_3$)$_2$))C(OH)(SO$_3$M)-H, Ac-FGA-NHCH(CH$_2$Ph)C(OH)(SO$_3$M)-H, Ac-FGV-NHCH(CH$_2$C$_6$H$_4$OH)C(OH)(SO$_3$M)-H, Ac-FGA-NHCH(CH$_2$CH$_2$SCH$_3$)(SO$_3$M)-H, Ac-WLV-NHCH(CH$_2$C$_6$H$_4$OH)C(OH)(SO$_3$M)-H, MeO-CO-VA-NHCH(CH$_2$CH(CH$_3$)$_2$))C(OH)(SO$_3$M)-H, MeNCO-VA-NHCH(CH$_2$CH(CH$_3$)$_2$))C(OH)(SO$_3$M)-H, MeO-CO-FGA-NHCH(CH$_2$CH(CH$_3$)$_2$))C(OH)(SO$_3$M)-H, MeO-CO-FGA-NHCH(CH$_2$Ph)-C(OH)(SO$_3$M)-H, MeSO$_2$-FGA-NHCH(CH$_2$CH(CH$_3$)$_2$))C(OH)(SO$_3$M)-H, MeSO$_2$-VA-NHCH(CH$_2$CH(CH$_3$)$_2$))C(OH)(SO$_3$M)-H, PhCH$_2$O(OH)(O)P-VA-NHCH(CH$_2$CH(CH$_3$)$_2$))—C(OH)(SO$_3$M)-H, EtSO$_2$-FGA-NHCH(CH$_2$CH(CH$_3$)$_2$))C(OH)(SO$_3$M)-H, PhCH$_2$SO$_2$—VA-NHCH(CH$_2$CH(CH$_3$)$_2$))C(OH)(SO$_3$M)-H, PhCH$_2$O(OH)(O)P-LA-NHCH(CH$_2$CH(CH$_3$)$_2$))—C(OH)(SO$_3$M)-H, PhCH$_2$O(OH)(O)P-FA-NHCH(CH$_2$CH(CH$_3$)$_2$))C(OH)(SO$_3$M)-H, MeO(OH)(O)P-LGA-NHCH(CH$_2$CH(CH$_3$)$_2$))C(OH)(SO$_3$M)-H, and F-urea-RV-NHCH(CH$_2$C$_6$H$_4$OH)C(OH)(SO$_3$M)-H where M=negative charge, H, Na, or K or another counter ion.

Subtilisin

Subtilisins is a sub-group of serine proteases. A serine protease is an enzyme which catalyzes the hydrolysis of peptide bonds, and in which there is an essential serine residue at the active site (White, Handler and Smith, 1973 "Principles of Biochemistry," Fifth Edition, McGraw-Hill Book Company, NY, pp. 271-272). Subtilisins include, preferably consist of, the I-S1 and I-S2 sub-groups as defined by Siezen et al., Protein Engng. 4 (1991) 719-737; and Siezen et al., Protein Science 6 (1997) 501-523. Because of the highly conserved structure of the active site of serine proteases, the subtilisin according to the invention may be functionally equivalent to the proposed sub-group designated subtilase by Siezen et al. (supra).

The subtilisin may be of animal, vegetable or microbial origin, including chemically or genetically modified mutants (protein engineered variants). Examples of subtilisins are those derived from *Bacillus*, e.g., subtilisin Novo, subtilisin Carlsberg, subtilisin BPN', subtilisin 309, subtilisin 147 and subtilisin 168 (described in WO 89/06279) and Protease PD138 (WO 93/18140). Examples are described in WO 98/020115, WO 01/44452, WO 01/58275, WO 01/58276, WO 03/006602 and WO 04/099401. Other examples are the variants described in WO 92/19729, WO 98/20115, WO 98/20116, WO 98/34946, WO 2011/036263 and mixtures of proteases.

Examples of commercially available subtilisins include Kannase™, Everlase™, Relase™, Esperase™, Alcalase™, Durazym™, Savinase™, Ovozyme™, Liquanase™, Coronase™, Polarzyme™, Pyrase™, Pancreatic Trypsin NOVO (PTN), Bio-Feed™ Pro and Clear-Lens™ Pro; Blaze (all available from Novozymes A/S, Bagsvaerd, Denmark). Other commercially available subtilisins include Ronozyme™ Pro, Maxatase™, Maxacal™, Maxapem™ Opticlean™, Properase™, Purafast™, Purafect™, Purafect Ox™, Purafact Prime™ Excellase™, FN2™, FN3™ and FN4™ (available from Genencor International Inc., Gist-Brocades, BASF, or DSM). Other examples are Primase™ and Duralase™. Blap R, Blap S and Blap X available from Henkel.

Second Enzyme

In addition to the subtilisin, the detergent composition may optionally comprise a second enzyme such as a lipase, a cutinase, an amylase, a carbohydrase, a cellulase, a pectinase, a pectate lyase, a mannanase, an arabinase, a galactanase, a xylanase, an oxidase, a laccase, and/or peroxidase. The composition may contain one, two or more non-subtilisin enzymes.

Lipase and Cutinase

Suitable lipases and cutinases include those of bacterial or fungal origin. Chemically modified or protein engineered mutants are included. Examples include lipase from *Thermomyces*, e.g., from *T. lanuginosus* (previously named *Humicola lanuginosa*) as described in EP 258 068 and EP 305 216, cutinase from *Humicola*, e.g. *H. insolens* as described in WO 96/13580, a *Pseudomonas* lipase, e.g., from *P. alcaligenes* or *P. pseudoalcaligenes* (EP 218 272), *P. cepacia* (EP 331 376), *P. stutzeri* (GB 1,372,034), *P. fluorescens, Pseudomonas* sp. strain SD 705 (WO 95/06720 and WO 96/27002), *P. wisconsinensis* (WO 96/12012), a *Bacillus* lipase, e.g., from *B. subtilis* (Dartois et al., 1993, *Biochemica et Biophysica Acta*, 1131: 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079, WO 97/07202, WO 00/060063, WO 2007/087508 and WO 2009/109500.

Preferred commercially available lipase enzymes include Lipolase™, Lipolase Ultra™ and Lipex™; Lecitase™, Lipolex™; Lipoclean™, Lipoprime™ (Novozymes A/S). Other commercially available lipases includes Lumafast (Genencor Int Inc); Lipomax (Gist-Brocades/Genencor Int Inc) and *Bacillus* sp lipase from Solvay.

Amylase

Suitable amylases (α and/or β) include those of bacterial or fungal origin. Chemically modified or protein engineered mutants are included. Amylases include, for example, α-amylases obtained from *Bacillus*, e.g., a special strain of *Bacillus licheniformis*, described in more detail in GB 1,296, 839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are Stainzyme; Stainzyme Plus; Duramyl™, Termamyl™, Termamyl Ultra; Natalase, Fungamyl™ and BAN™ (Novozymes A/S), Rapidase™ and Purastar™ (from Genencor International Inc.).

Lyases

The pectate lyase may be a wild-type enzymes derived from *Bacillus*, particularly *B. lichemiformis* or *B. agaradhaerens*, or a variant derived of any of these, e.g., as described in U.S. Pat. No. 6,124,127, WO 1999/027083, WO 1999/027084, WO 2002/006442, WO 2002/092741, WO 2003/095638, A commercially available pectate lyase is XPect; Pectawash and Pectaway (Novozymes A/S).

Mannanase

The mannanase may be an alkaline mannanase of Family 5 or 26. It may be a wild-type from *Bacillus* or *Humicola*, particularly *B. agaradhaerens, B. licheniformis, B. halodurans, B. clausii*, or *H. insolens*. Suitable mannanases are described in WO 1999/064619. A commercially available mannanase is Mannaway (Novozymes A/S).

Cellulase

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having color care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and WO 99/01544.

Commercially available cellulases are Celluzyme, Celluclean; Endloase; Carezyme; Renozyme; whitezyme (Novozymes A/S).

Preparation of Peptide Aldehyde and Hydrosulfite/Bisulfite Adduct

The peptide aldehyde may be converted into a water-soluble hydrosulfite adduct by reaction with sodium bisulfite, as described in textbooks, e.g. March, J. Advanced Organic Chemistry, fourth edition, Wiley-Interscience, US 1992, p 895.

The conversion into a hydrosulfite adduct is reversible (Ex J. Am. Chem. Soc. 1978, 100, 1228). Thus, the adduct may partly or fully revert to release the peptide aldehyde in a liquid detergent, in a liquid subtilisin formulation, or in the wash water.

The peptide aldehyde in question may be prepared by known methods, e.g., as described in as described in U.S. Pat. Nos. 4,703,036, 4,478,745 or 5,578,574 by omitting a final drying step, or it may be prepared by any of the methods reviewed in *J. Pept. Sci.* 2007; 13; 1-15 or exemplified in Synthesis 1983, 676. The peptide aldehyde can be crude or purified, isolated as a solid or kept in solution by an organic solvent.

An aqueous solution of the bisulfite adduct may be prepared by reacting the corresponding peptide aldehyde with an aqueous solution of sodium bisulfite (sodium hydrogen sulfite, $NaHSO_3$); potassium bisulfite ($KHSO_3$) by known methods, e.g., as described in WO 98/47523; U.S. Pat. Nos. 6,500,802; 5,436,229; J. Am. Chem. Soc. 1978, 100, 1228; Org. Synth., Coll. Vol. 7: 361.

Detergent Composition

The detergent could be granular or liquid detergent. The liquid detergent is in a physical form, which is not solid (or gas); it may be a pourable liquid, a pourable gel or a non-pourable gel. It may be either isotropic or structured, preferably isotropic. It includes formulations useful for washing in automatic washing machines or for hand washing. The detergent contains at least one surfactant. The detergent may also include a builder.

The particulate detergent composition may be a granulate or powder, or a powder/granulate pressed to a tablet, briquette. The composition may be in the form of a tablet, bar or pouch, including multi-compartment pouches. The composition can be in the form of a powder, for example a free-flowing powder, such as an agglomerate, spray-dried powder, encapsulate, extrudate, needle, noodle, flake, or any combination thereof.

Detergent ingredients can be separated physically from each other by compartments in water dissolvable pouches or in different layers of tablets (see Unit Dose below). Thereby negative storage interaction between components can be avoided. Different dissolution profiles of each of the compartments can also give rise to delayed dissolution of selected components in the wash solution.

Pouches can be of any form, shape and material which is suitable for holding the composition, e.g., without allowing the release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivates thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxypropyl methyl cellulose (HPMC). Preferably the level of polymer in the film for example PVA is at least about 60%. Preferred average molecular weight will typically be about 20,000 to about 150,000. Films can also be a blend compositions comprising hydrolytically degradable and water soluble polymer blends such as polyactide and polyvinyl alcohol (known under the Trade reference M8630 as sold by Chris Craft In. Prod. Of Gary, Ind., US) plus plasticizers like glycerol, ethylene glycerol, Propylene glycol, sorbitol and mixtures thereof. The pouches can comprise a solid laundry cleaning composition or part components and/or a liquid cleaning composition or part components separated by the water soluble film. The compartment for liquid components can be different in composition than compartments containing solids (see e.g., US 2009/0011970).

The choice of detergent components may include, for textile care, the consideration of the type of textile to be cleaned, the type and/or degree of soiling, the temperature at which cleaning is to take place, and the formulation of the detergent product. Although components mentioned below are categorized by general header according to a particular functionality, this is not to be construed as a limitation, as a component may comprise additional functionalities as will be appreciated by the skilled artisan.

In one embodiment, the stabilized subtilisin composition of the invention may be added to a detergent composition in an amount corresponding to 0.001-100 mg of protein, such as 0.01-100 mg of protein, preferably 0.005-50 mg of protein, 0.01-25 mg of protein, even more preferably 0.05-10 mg of protein, most preferably 0.05-5 mg of protein, and even most preferably 0.01-1 mg of protein per liter of wash liquor.

Unit Dose

A unit dose product is the packaging of a single dose in a non-reusable container. It is increasingly used in detergents for laundry and dish wash. A detergent unit dose product is the packaging (e.g., in a pouch made from a water soluble film) of the amount of detergent used for a single wash.

In one aspect, the detergent composition is in unit dose form. Detergent products in unit dose form include tablets, capsules, sachets, pouches, etc. In one aspect, for use herein are tablets wrapped with a water-soluble film and water-soluble pouches. The weight of the detergent composition of the invention is from about 10 to about 25 grams, from about 12 to about 24 grams or even from 14 to 22 grams. These weights are extremely convenient for automatic dishwashing detergent product dispenser fit. In the cases of unit dose products having a water-soluble material enveloping the detergent composition, the water-soluble material is not considered as part of the composition. In one aspect, the unit dose form is a water-soluble pouch (i.e., water-soluble film enveloping a detergent composition), in one aspect, a multi-compartment pouch having a plurality of films forming a plurality of compartments. This configuration contributes to the flexibility and optimization of the composition. It allows for the separation and controlled release of different ingredients. In one aspect, one compartment contains a detergent composition in solid form and another compartment contains a detergent composition in liquid form.

In one aspect, multi-compartment pouch embodiments two different compartments could contain two different cleaning agents. In one aspect, the films of these two compartments have different dissolution profiles, allowing the release of the same or different agents at different times. For example, the agent from one compartment (first compartment) can be delivered early in the washing process to help with soil removal and a second agent from another compartment (second compartment) can be delivered at least two minutes, or even at least five minutes later than the agent from the first compartment.

In one aspect, a multi-compartment pouch comprising two side-by-side compartments superposed onto another compartment wherein at least two different compartments contain two different detergent compositions is disclosed.

A multi-compartments pack is formed by a plurality of water-soluble enveloping materials which form a plurality of compartments, one of the compartments would contain some or all ingredients of the detergent composition, another compartment can contain a liquid composition, the liquid composition can be aqueous (i.e. comprises more than 10 percent of water by weight of the liquid composition) and the compartment can be made of warm water soluble material. In one embodiment, one compartment is made of a cold water soluble material. It allows for the separation and controlled release of different ingredients. In other embodiments all the compartments are made of warm water soluble material.

Suitable packs comprise at least two side-by-side compartments superposed (i.e. placed above) onto another compartment, especially suitable are pouches. This disposition contributes to the compactness, robustness and strength of the pack, additionally, it minimises the amount of water-soluble material required. It only requires three pieces of material to form three compartments. The robustness of the pack allows also for the use of very thin films without compromising the physical integrity of the pack. The pack is also very easy to use because the compartments do not need to be folded to be used in machine dispensers of fix geometry. At least two of the compartments of the pack contain two different detergent compositions. By "different compositions" herein is meant detergent compositions that differ in at least one ingredient.

In one aspect, at least one of the compartments contains a solid detergent composition and another compartment an aqueous liquid detergent composition, the compositions are typically in a solid to liquid weight ratio of from about 20:1 to about 1:20, from about 18:1 to about 2:1 or from about 15:1 to about 5:1. This kind of pack is very versatile because it can accommodate compositions having a broad spectrum of values of solid:liquid ratio. Pouches having a high solid:liquid ratio because many of the detergent ingredients are particularly suitable for use in solid form, in one aspect in powder form. The ratio solid:liquid defined herein refers to the relationship between the weight of all the solid compositions and the weight of all the liquid compositions in the pack.

Suitable solid:liquid weight ratios are from about 2:1 to about 18:1, or from about 5:1 to about 15:1. These weight ratios are suitable in cases in which most of the ingredients of the detergent are in liquid form.

In one aspect, the two side-by-side compartments contain liquid detergent compositions, which can be the same or different and another compartment contains a solid detergent composition, for example in powder form, in one aspect, a densified powder. The solid composition contributes to the strength and robustness of the pack.

For dispenser fit reasons, especially in an automatic dishwasher, the unit dose form products herein have a square or rectangular base and a height of from about 1 to about 5 cm, or from about 1 to about 4 cm. In one aspect, the weight of the solid composition is from about 5 to about 20 grams, or from about 10 to about 15 grams and the weight of the liquid compositions is from about 0.5 to about 4 grams, or from about 0.8 to about 3 grams. In one aspect, at least two of the films which form different compartments have different solubilities, under the same conditions. This enables the release of the compositions which they partially or totally envelope at different times.

Controlled release of the ingredients of a multi-compartment pouch can be achieved by modifying the thickness of the film and/or the solubility of the film material. The solubility of the film material can be delayed by for example crosslinking the film as described in WO 2002/102955. Other water-soluble films designed for rinse release are described in U.S. Pat. Nos. 4,765,916 and 4,972,017. Waxy coating (see U.S. Pat. No. 5,453,216) of films can help with rinse release. pH controlled release means are described in U.S. Pat. No. 5,453,216, in particular amino-acetylated polysaccharide having selective degree of acetylation.

Other means of obtaining delayed release by multi-compartment pouches with different compartments, where the compartments are made of films having different solubility are taught in U.S. Pat. No. 6,727,215.

Surfactants

The detergent composition may comprise one or more surfactants, which may be anionic and/or cationic and/or non-ionic and/or semi-polar and/or zwitterionic, or a mixture thereof. In a particular embodiment, the detergent composition includes a mixture of one or more nonionic surfactants and one or more anionic surfactants but can also be used individually.

The surfactant(s) is typically present at a level of from about 0.1% to 60% by weight, such as about 1% to about 40%, or about 3% to about 20%, or about 3% to about 10%. The surfactant(s) is chosen based on the desired cleaning application, and includes any conventional surfactant(s) known in the art. Any surfactant known in the art for use in detergents may be utilized.

Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates, including sodium lauryl ether sulfate (SLES), soaps or fatty acids; secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or soap, and combinations thereof.

When included therein the detergent will usually contain from about 1% to about 40% by weight, such as from about 5% to about 30%, including from about 5% to about 15%, or from about 20% to about 25% of an anionic surfactant.

Non-limiting examples of non-ionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamide (PFAM), polyhydroxy alkyl fatty acid amides, or N-acyl N-alkyl derivatives of glucosamine (glucamides, GA, or fatty acid glucamide, FAGA), as well as products available under the trade names SPAN and TWEEN, and combinations thereof.

When included therein the detergent will usually contain from about 0.2% to about 40% by weight of a non-ionic surfactant, for example from about 0.5% to about 30%, in particular from about 1% to about 20%, from about 3% to about 10%, such as from about 3% to about 5%, or from about 8% to about 12%.

Builders

The detergent composition may contain about 0-65% by weight of a detergent builder or co-builder, or a mixture thereof. In a dish wash detergent, the level of builder is typically 40-65%, particularly 50-65%. The builder and/or co-builder may particularly be a chelating agent that forms water-soluble complexes with Ca and Mg. Any builder and/or co-builder known in the art for use in laundry detergents may be utilized. Non-limiting examples of builders include zeolites, diphosphates (pyrophosphates), triphosphates such as sodium triphosphate (STP or STPP), nitrilotriacetic acid, ethylenediaminetetraacetic acid (EDTA), diethylenetriaminepentaacetic acid, alkyl- or alkenylsuccinic acid, carbonates such as sodium carbonate, soluble silicates such as sodium metasilicate, layered silicates (e.g., SKS-6 from Hoechst), ethanolamines such as 2-aminoethan-1-ol (MEA), iminodiethanol (DEA) and 2,2',2"-nitrilotriethanol (TEA), and carboxymethylinulin (CMI), and combinations thereof.

The builder may be a strong builder such as methyl glycine diacetic acid ("MGDA") or N,N-Dicarboxymethyl glutamic acid tetrasodium salt (GLDA); it may be a medium builder such as sodium tri-poly-phosphate (STPP), or it may be a weak builder such as sodium citrate.

Bleaching System

The detergent composition may contain 0-50% by weight of a bleaching system. Any bleaching system known in the art for use in laundry detergents may be utilized. Suitable bleaching system components include bleaching catalysts, photobleaches, bleach activators, sources of hydrogen peroxide such as sodium percarbonate and sodium perborates, preformed peracids and mixtures thereof. Suitable preformed peracids include, but are not limited to, peroxycarboxylic acids and salts, percarbonic acids and salts, perimidic acids and salts, peroxymonosulfuric acids and salts, for example, Oxone (R), and mixtures thereof. Non-limiting examples of bleaching systems include peroxide-based bleaching systems, which may comprise, for example, an inorganic salt, including alkali metal salts such as sodium salts of perborate (usually mono- or tetra-hydrate), percarbonate, persulfate, perphosphate, persilicate salts, in combination with a per-acid-forming bleach activator. By Bleach activator is meant herein a compound which reacts with peroxygen bleach like hydrogen peroxide to form a Peracid. The peracid thus formed constitutes the activated bleach. Suitable bleach activators to be used herein include those belonging to the class of esters amides, imides or anhydrides, Suitable examples are tetracetyl athylene diamine (TAED), sodium 3,5,5 trimethyl hexanoyloxybenzene sulphonat, diperoxy dodecanoic acid, 4-(dodecanoyloxy)benzenesulfonate (LOBS), 4-(decanoyloxy)benzenesulfonate, 4-(decanoyloxy)benzoate (DOBS), 4-(3,5,5-trimethylhexanoyloxy)benzenesulfonate (ISONOBS), tetraacetylethylenediamine (TAED) and 4-(nonanoyloxy)benzenesulfonate (NOBS), and/or those disclosed in WO98/17767. A particular family of bleach activators of interest was disclosed in EP624154 and particularly preferred in that family is acetyl triethyl citrate (ATC). ATC or a short chain triglyceride like Triacin has the advantage that it is environmental friendly as it eventually degrades into citric acid and alcohol. Furthermore acethyl triethyl citrate and triacetin has a good hydrolytical stability in the product upon storage and it is an efficient bleach activator. Finally ATC provides a good building capacity to the laundry additive. Alternatively, the bleaching system may comprise peroxyacids of, for example, the amide, imide, or sulfone type. The bleaching system may also comprise peracids such as 6-(phthaloylamino)percapronic acid (PAP). The bleaching system may also include a bleach catalyst.

Other ingredients of the detergent composition, which are all well-known in art, include hydrotropes, fabric hueing agents, anti-foaming agents, soil release polymers, anti-redeposition agents etc.

Methods and Compositions

In a first aspect, the present invention provides a composition, which comprises a subtilisin and a peptide aldehyde hydrosulfite adduct having the formula $X-B^1-NH-CHR-CHOH-SO_3M$, wherein:

a) M is H (hydrogen) or an alkali metal;
b) R is a group such that NH—CHR—CO is an L or D-amino acid residue;
c) $B^1$ is one amino acid residue; and
d) X consists of one or more amino acid residues, optionally comprising an N-terminal protection group.

In an embodiment, R is a group such that NH—CHR—CO is an L or D-amino acid residue of Tyr, m-tyrosine, 3,4-dihydroxyphenylalanine, Phe, Val, Met, Nva, Leu, Ile or Nle.

In an embodiment, $B^1$ is a residue of Ala, Cys, Gly, Pro, Ser, Thr, Val, Nva, or Nle.

In an embodiment, X is $B^2$, $B^3-B^2$, $Z-B^2$, or $Z-B^3-B^2$, wherein $B^2$ and $B^3$ each represents one amino acid residue, and Z is an N-terminal protection group. Preferably, $B^2$ is a residue of Val, Gly, Ala, Arg, Leu, Phe or Thr. Preferably, $B^3$ is a residue of Phe, Tyr, Trp, Phenylglycine, Leu, Val, Nva, Nle or Ile.

In an embodiment, Z is benzyloxycarbonyl (Cbz), p-methoxybenzyl carbonyl (MOZ), benzyl (Bn), benzoyl (Bz), p-methoxybenzyl (PMB), p-methoxyphenyl (PMP), formyl, acetyl (Ac), methyloxy, or methyloxycarbonyl.

In an embodiment, the composition is in liquid or granular form. Preferably, the composition is a detergent further comprising a surfactant.

In an embodiment, the composition further comprises a second enzyme, particularly a lipase, a cutinase, an amylase, a carbohydrase, a cellulase, a pectinase, a pectate lyase, a mannanase, an arabinase, a galactanase, a xylanase, an oxidase, a laccase or a peroxidase.

In another aspect, the invention provides a method of preparing the composition of the invention, as described above, which method comprises mixing a subtilisin, an aqueous solution comprising a peptide aldehyde hydrosulfite adduct having the formula $X-B^1-NH-CHR-CHOH-SO_3M$, as described above, and optionally a surfactant.

In yet another aspect, the invention provides a compound for use in the composition of the invention, which compound is a peptide aldehyde hydrosulfite adduct having the formula $X-B^1-NH-CHR-CHOH-SO_3M$, wherein M and X are defined as described above, $B^1$ is an amino acid residue which is different from proline (Pro), and R is a group such that NH—CHR—CO is an L or D-amino acid residue of Tyr, m-tyrosine, 3,4-dihydroxyphenylalanine, Phe, Val, Met, Nva or Nle.

In an embodiment, the compound is Cbz-RA-NHCH(CH$_2$C$_6$H$_4$OH)C(OH)(SO$_3$M)-H, Ac-GA-NHCH(CH$_2$C$_6$H$_4$OH)C(OH)(SO$_3$M)-H, Cbz-GA-NHCH(CH$_2$C$_6$H$_4$OH)C(OH)(SO$_3$M)-H, Cbz-GG-NHCH(CH$_2$C$_6$H$_4$OH)C(OH)(SO$_3$M)-H, Cbz-RV-NHCH(CH$_2$C$_6$H$_4$OH)C(OH)(SO$_3$M)-H, Cbz-LV-NHCH(CH$_2$C$_6$H$_4$OH)C(OH)(SO$_3$M)-H, Ac-LGA-NHCH(CH$_2$C$_6$H$_4$OH)C(OH)(SO$_3$M)-H, Ac-FGA-NHCH(CH$_2$C$_6$H$_4$OH)C(OH)(SO$_3$M)-H, Ac-YGA-NHCH(CH$_2$C$_6$H$_4$OH)C(OH)(SO$_3$M)-H, Ac-FGV-NHCH(CH$_2$C$_6$H$_4$OH)C(OH)(SO$_3$M)-H, or Ac-WLV-NHCH(CH$_2$C$_6$H$_4$OH)C(OH)(SO$_3$M)-H, wherein Ac is acetyl and Cbz is benzyloxycarbonyl.

In yet another aspect, the invention provides a compound for use in the composition of the invention, which compound is a peptide aldehyde hydrosulfite adduct having the formula $X-B^1-NH-CHR-CHOH-SO_3M$, wherein M, R and X are defined as described above, and wherein $B^1$ is an amino acid residue of alanine (Ala), cysteine (Cys), glycine (Gly), serine (Ser), threonine (Thr), valine (Val), norvaline (Nva) and norleucine (Nle).

In an embodiment, the compound is Cbz-GA-NHCH(CH$_2$CH(CH$_3$)$_2$))C(OH)(SO$_3$M)-H, Cbz-VA-NHCH(CH$_2$CH(CH$_3$)$_2$))C(OH)(SO$_3$M)-H, Cbz-GA-NHCH(CH$_2$Ph)C(OH)(SO$_3$M)-H, Cbz-GA-NHCH(CH(CH$_3$)$_2$)C(OH)(SO$_3$M)-H, Cbz-GG-NHCH(CH$_2$Ph)C(OH)(SO$_3$M)-H, Ac-FGA-NHCH(CH$_2$CH(CH$_3$)$_2$))C(OH)(SO$_3$M)-H, Ac-FGA-NHCH($CH_2$Ph)C(OH)($SO_3$M)-H, Ac-FGA-NHCH($CH_2CH_2SCH_3$)($SO_3$M)-H, MeO-CO-VA-NHCH($CH_2$CH($CH_3$)$_2$)C(OH)($SO_3$M)-H, MeNCO-VA-NHCH($CH_2$CH($CH_3$)$_2$)C(OH)($SO_3$M)-H, MeO-CO-FGA-NHCH($CH_2$CH($CH_3$)$_2$))—C(OH)($SO_3$M)-H, MeO-CO-FGA-NHCH($CH_2$Ph)C(OH)($SO_3$M)-H, MeSO2-FGA-NHCH($CH_2$CH($CH_3$)$_2$)C(OH)($SO_3$M)-H, MeSO2-VA-NHCH($CH_2$CH($CH_3$)$_2$)C(OH)($SO_3$M)-H, PhCH2O(OH)(O)P-VA-NHCH($CH_2$CH($CH_3$)$_2$))C(OH)($SO_3$M)-H, EtSO2-FGA-NHCH($CH_2$CH($CH_3$)$_2$))C(OH)($SO_3$M)-H, PhCH2SO2-VA-NHCH($CH_2$CH($CH_3$)$_2$))C(OH)($SO_3$M)-H, PhCH2O(OH)(O)P-LA-NHCH($CH_2$CH($CH_3$)$_2$))C(OH)($SO_3$M)-H, PhCH2O(OH)(O)P-FA-NHCH($CH_2$CH($CH_3$)$_2$))C(OH)($SO_3$M)-H, and MeO(OH)(O)P-LGA-NHCH($CH_2$CH($CH_3$)$_2$))—C(OH)($SO_3$M)-H, wherein Ac is acetyl and Cbz is benzyloxycarbonyl.

In yet another aspect, the invention provides a compound for use in the composition of the invention, which compound is a peptide aldehyde hydrosulfite adduct having the formula X—$B^1$—NH—CHR—CHOH—$SO_3$M; wherein R and M are defined as described above; $B^1$ represents one amino acid residue which is different from proline (Pro); X is $B^2$, $B^3$—$B^2$, Z—$B^2$, Z—$B^3$—$B^2$, wherein $B^3$ and $B^2$ each represents one amino acid residue, and Z is an N-terminal protection group; and wherein $B^2$ is Gly, Thr or Val.

In yet another aspect, the invention provides a compound for use in the composition of the invention, which compound is a peptide aldehyde hydrosulfite adduct having the formula X—$B^1$—NH—CHR—CHOH—$SO_3$M; wherein R and M are defined as described above; $B^1$ represents one amino acid residue which is different from proline (Pro); X is $B^3$—$B^2$, Z—$B^3$—$B^2$, wherein $B^3$ and $B^2$ each represents one amino acid residue, and Z is an N-terminal protection group; and wherein $B^3$ is Phe, Tyr, Trp, Phenylglycine, Leu, Val, Nva, Nle or Ile.

EXAMPLES

Chemicals used as buffers and substrates were commercial products of at least reagent grade.

Example 1

Preparation of a Hydrosulfite Adduct of a Peptide Aldehyde

A peptide aldehyde with the formula X—$B^1$—$B^0$—H, as described above, is converted into the corresponding bisulfite adduct. To a stirred suspension of 1 mmol X—$B^1$—$B^0$—H in 8 ml ethyl acetate at ambient temperature is added dropwise 1.06 mmol sodium bisulfite (114 mg) in 6 ml water and then the reaction is stirred for 2 hours. The aqueous phase is isolated and the organic layer is washed with 2×2 ml water. The combined aqueous phases are freeze dried giving X—$B^1$—NH—CHR—CHOH—$SO_3$Na (predicted yield 66%) as a white powder.

Example 2

Preparation of a Liquid Formulation of a Peptide Aldehyde Hydrosulfite Adduct 4 mmol of solid X—$B^1$—NH—CHR—CHOH—$SO_3$Na is dissolved in 6 g demineralized water and stirred for 30 min at 35° C. and subsequently cooled down giving a 25% aqueous solution of X—$B^1$—NH—CHR—CHOH—$SO_3$Na. Alternatively the aqueous phase from the above synthesis could be readily used for enzyme stabilization in the following step and this solution is approx. 3% (w/w).

Example 3

Preparation of a Stabilized Subtilisin Formulation Comprising Subtilisin and Peptide Aldehyde Hydrosulfite Adduct To a commercially available Savinase 16L™ (Novozymes A/S, Bagsvaerd, Denmark) 0.9% X—$B^1$—NH—CHR—CHOH—$SO_3$Na is added by using 3.6% of the above 25% aqueous solution.

Example 4

Stabilization of Subtilisin by Hydrosulfite Adduct

General experimental details: Detergents with a subtilisin (Savinase 16L) and a lipase (Lipex 100L) with or without X—$B^1$—NH—CHR—CHOH—$SO_3$Na (the peptide aldehyde hydrosulfite adduct can be added separately to the detergent containing the subtilisin) are placed in closed glasses at −18° C.; 35° C. and 40° C. Residual activities of protease and lipase are measured after different times using standard analytical methods (protease by hydrolysis of N,N-dimethylcasein at 40° C., pH 8.3 and lipase by hydrolysis of pNp-valerate at 40° C., pH 7.7). Similar trials can be made with addition of subtilisin to a detergent already containing suitable amounts of the peptide aldehyde hydrosulfite adduct. Similar results can be obtained with all the mentioned peptide aldehyde bisulfite adducts.

As an example of detergent composition with a stabilized subtilisin formulation, the composition described in Table 1 was made.

TABLE 1

| Detergent composition. | |
|---|---|
| Component | % (w/w) |
| Sodium alkylethoxy sulphate (C9-15, 2EO) | 6.0 |
| Sodium dodecyl benzene sulfonate | 3.0 |
| Sodium toluene sulfonate | 3.0 |
| Oleic acid | 2.0 |
| Primary alcohol ethoxylate (C12-15, 7EO) | 3.0 |
| Primary alcohol ethoxylate (C12-15, 3EO) | 2.5 |
| Ethanol | 0.5 |
| Monopropylene glycol | 2.0 |
| Tri-sodium citrate 2$H_2$O | 4.0 |
| Triethanol amine | 0.4 |
| pH adjusted to 8.5 with NaOH | |
| Stabilized Savinase formulation with X—$B^1$—NH—CHR—CHOH—$SO_3$Na; or Savinase 16L for comparison | 0.5 |
| Lipex 100L ™ (available from Novozymes A/S) | 0.5 |
| Water | ad 100% |

In Table 2 are shown the results obtained with X=Cbz-Gly; $B^1$=Ala; R=—$CH_2$-p($C_6H_4$)—OH; stability measured after one week incubation at 40° C. in the detergent described in Table 1.

TABLE 2

| Remaining protease activity after one week incubation at 40° C. in the detergent described in Table 1. | |
|---|---|
| Amount of inhibitor added to the detergent | Protease stability (remaining activity) |
| none | 12% |
| 7 ppm | 52% |
| 14 ppm | 77% |
| 18 ppm | 80% |

The results demonstrate stabilization of the subtilisin by the addition of a hydrosulfite adduct of a peptide aldehyde.

Example 5

Stabilization of Subtilisin and Lipase

As an example of a detergent composition with a stabilized subtilisin formulation, the composition described in Table 3 was made.

TABLE 3

Detergent composition.

| Component | % (w/w) |
|---|---|
| Sodium dodecyl benzene sulfonate | 6.0 |
| NaOH | 1.4 |
| Soy fatty acid (Edenor SJ) | 3.0 |
| Coco fatty acid (Radiacid 0631) | 2.5 |
| Primary alcohol ethoxylate (C13, 8EO) | 5.0 |
| Ethanol | 5.0 |
| Monopropylene glycol | 5.0 |
| Tri-sodium citrate 2H$_2$O | 0.5 |
| Triethanol amine | 2.0 |
| Phosphonat-Dequest 2066 C2 | 3.0 |
| pH adjusted to 8.4 with additional NaOH if necessary | |
| Subtilisin: Savinase, stabilized with X—B$^1$—NH—CHR—CHOH—SO$_3$Na; or with 4-formylphenyl boronic acid; or without stabilizer for comparison | 0.75 |
| Lipase: Lipex 100L ™ (available from Novozymes A/S) | 0.15 |
| Water | ad 100% |

In Table 4 are shown the results measured after two weeks incubation at 35° C. in the detergent described in Table 3.

TABLE 4

Remaining activity of Subtilisin (protease) and Lipase after 2 weeks incubation at 35° C. in the detergent described in Table 3.

| Inhibitor | Inhibitor in detergent | Subtilisin | Lipase |
|---|---|---|---|
| none | — | 2% | 1% |
| 4-formylphenyl boronic acid (prior art) | 128 ppm | 8% | 2% |
| X = Cbz—Gly; B$^1$ = Ala; R = —CH$_2$—p(C$_6$H$_4$)—OH | 21 ppm | 63% | 18% |

The results demonstrate that the addition of a hydrosulfite adduct of a peptide aldehyde can stabilize the subtilisin and the second enzyme (lipase), and that it is much more effective than the prior-art stabilizer.

Example 6

Stabilization of Subtilisin and Lipase

As yet another example of a detergent with a stabilized subtilisin formulation, the composition described in Table 5 was made.

TABLE 5

Detergent composition.

| Component | % (w/w) |
|---|---|
| Commercial non-enzymatic detergent. Liquid EU 2x dosed. Purchased in UK, 2009 | 98.2 |
| Subtilisin | 1.4 |
| Lipase: Lipoclean 2000L (available from Novozymes NS) | 0.4 |

In Table 6 are shown the results measured after 4 weeks incubation at 37° C., and after 8 weeks incubation at 30° C., in the detergent described in Table 5.

TABLE 6

Remaining activity of Subtilisin (protease) and Lipase after 4 weeks incubation at 37° C., or after 8 weeks incubation at 30° C. in the detergent described in Table 5.

| Inhibitor | Subtilisin | Amount of inhibitor added to detergent | Subtilisin 4 weeks at 37° C. | Lipase 8 weeks at 30° C. |
|---|---|---|---|---|
| none | Coronase 48L | 0 | 69% | 28% |
| X = Cbz—Gly; B$^1$ = Ala; R = —CH$_2$—p(C$_6$H$_4$)—OH | Coronase 48L | 59 ppm | 80% | 61% |
| none | Liquanase 2.5L | 0 | 43% | 0% |
| X = Cbz—Gly; B$^1$ = Ala; R = —CH$_2$—p(C$_6$H$_4$)—OH | Liquanase 2.5L | 34 ppm | 83% | 27% |

The results confirm that the addition of a hydrosulfite adduct of a peptide aldehyde can stabilize the subtilisin and the second enzyme (lipase) for various subtilisins.

The invention claimed is:

1. A composition, which comprises a subtilisin and a peptide aldehyde hydrosulfite adduct having the formula X—B$^1$—NH—CHR—CHOH—SO$_3$M, wherein:
   a) M is H (hydrogen) or an alkali metal;
   b) R is a group such that NH—CHR—CO is an L or D-amino acid residue;
   c) B$^1$ is one amino acid residue; and
   d) X consists of one or more amino acid residues, optionally comprising an N-terminal protection group.

2. The composition of claim 1 wherein R is a group such that NH—CHR—CO is an L or D-amino acid residue of Tyr, m-tyrosine, 3,4-dihydroxyphenylalanine, Phe, Val, Met, Nva, Leu, Ile or Nle.

3. The composition of claim 1 wherein B$^1$ is a residue of Ala, Cys, Gly, Pro, Ser, Thr, Val, Nva, or Nle.

4. The composition of claim 1 wherein X is B$^2$, B$^3$—B$^2$, Z—B$^2$, or Z—B$^3$—B$^2$, wherein B$^2$ and B$^3$ each represents one amino acid residue, and Z is an N-terminal protection group.

5. The composition of claim 4 wherein B$^2$ is a residue of Val, Gly, Ala, Arg, Leu, Phe or Thr.

6. The composition of claim 4 wherein B$^3$ is a residue of Phe, Tyr, Trp, Phenylglycine, Leu, Val, Nva, Nle or Ile.

7. The composition of claim 4 wherein Z is benzyloxycarbonyl (Cbz), p-methoxybenzyl carbonyl (MOZ), benzyl (Bn), benzoyl (Bz), p-methoxybenzyl (PMB), p-methoxyphenyl (PMP), formyl, acetyl (Ac), methyloxy, or methyloxycarbonyl.

8. The composition of claim 1 which is in liquid or granular form.

9. The composition of claim 1 which is a detergent further comprising a surfactant.

10. The composition of claim 1 which further comprises a second enzyme, particularly a lipase, a cutinase, an amylase, a carbohydrase, a cellulase, a pectinase, a pectate lyase, a mannanase, an arabinase, a galactanase, a xylanase, an oxidase, a laccase or a peroxidase.

11. A method of preparing the composition of claim 1, which method comprises mixing a subtilisin, an aqueous solution comprising a peptide aldehyde hydrosulfite adduct having the formula X—B$^1$—NH—CHR—CHOH— SO$_3$M, wherein M, R, B$^1$ and X are defined as in claim 1, and optionally a surfactant.

12. A peptide aldehyde hydrosulfite adduct compound having the formula X—B$^1$—NH—CHR—CHOH—SO$_3$M, wherein M is H (hydrogen) or an alkali metal and X consists of one or more amino acid residues, optionally comprising an N-terminal protection group B$^1$ is an amino acid residue which is different from proline (Pro), and R is a group such that NH—CHR—CO is an L or D-amino acid residue of Tyr, m-tyrosine, 3,4-dihydroxyphenylalanine, Phe, Val, Met, Nva or Nle.

13. The compound of claim 12, which is Cbz-RA-NHCH(CH$_2$C$_6$H$_4$OH)—C(OH)(SO$_3$M)-H, Ac-GA-NHCH(CH$_2$C$_6$H$_4$OH)C(OH)(SO$_3$M)-H, Cbz-GA-NHCH(CH$_2$C$_6$H$_4$OH)—C(OH)(SO$_3$M)-H, Cbz-GG-NHCH(CH$_2$C$_6$H$_4$OH)C(OH)(SO$_3$M)-H, Cbz-RV-NHCH(CH$_2$C$_6$H$_4$OH)C(OH)(SO$_3$M)-H, Cbz-LV-NHCH(CH$_2$C$_6$H$_4$OH)—C(OH)(SO$_3$M)-H, Ac-LGA-NHCH(CH$_2$C$_6$H$_4$OH)—C(OH)(SO$_3$M)-H, Ac-FGA-NHCH(CH$_2$C$_6$H$_4$OH)C(OH)(SO$_3$M)-H, Ac-YGA-NHCH(CH$_2$C$_6$H$_4$OH)C(OH)(SO$_3$M)-H, Ac-FGV-NHCH(CH$_2$C$_6$H$_4$OH)—C(OH)(SO$_3$M)-H, or Ac-WLV-NHCH(CH$_2$C$_6$H$_4$OH)—C(OH)(SO$_3$M)-H, wherein Ac is acetyl and Cbz is benzyloxycarbonyl.

14. A peptide aldehyde hydrosulfite adduct compound having the formula X—B$^1$—NH—CHR—CHOH—SO$_3$M, wherein M is H (hydrogen) or an alkali metal, R is a group such that NH—CHR—CO is an L or D-amino acid residue and X consists of one or more amino acid residues, optionally comprising an N-terminal protection group, and wherein B$^1$ is an amino acid residue of alanine (Ala), cysteine (Cys), glycine (Gly), serine (Ser), threonine (Thr), valine (Val), norvaline (Nva) and norleucine (Nle).

15. The compound of claim 14, which is Cbz-GA-NHCH(CH$_2$CH(CH$_3$)$_2$))C(OH)(SO$_3$M)-H, Cbz-VA-NHCH(CH$_2$CH(CH$_3$)$_2$))—C(OH)(SO$_3$M)-H, Cbz-GA-NHCH(CH$_2$Ph)C(OH)(SO$_3$M)-H, Cbz-GA-NHCH(CH(CH3)2)-C(OH)(SO$_3$M)-H, Cbz-GG-NHCH(CH$_2$Ph)-C(OH)(SO$_3$M)-H, Ac-FGA-NHCH(CH$_2$CH(CH$_3$)$_2$))C(OH)(SO$_3$M)-H, Ac-FGA-NHCH(CH$_2$Ph)C(OH)(SO$_3$M)-H, Ac-FGA-NHCH—(CH$_2$CH$_2$SCH$_3$)—(SO$_3$M)-H, MeO-CO-VA-NHCH—(CH$_2$CH(CH$_3$)$_2$))C(OH)(SO$_3$M)-H, MeNCO-VA-NHCH(CH$_2$CH(CH$_3$)$_2$))C(OH)(SO$_3$M)-H, MeO-CO-FGA-NHCH(CH$_2$CH(CH$_3$)$_2$))—C(OH)(SO$_3$M)-H, MeO-CO-FGA-NHCH(CH$_2$Ph)-C(OH)(SO$_3$M)-H, MeSO$_2$-FGA-NHCH(CH$_2$CH(CH$_3$)$_2$))—C(OH)(SO$_3$M)-H, MeSO$_2$-VA-NHCH(CH$_2$CH(CH$_3$)$_2$))—C(OH)(SO$_3$M)-H, PhCH$_2$O(OH)(O)P-VA-NHCH(CH$_2$CH(CH$_3$)$_2$))—C(OH)(SO$_3$M)-H, EtSO$_2$-FGA-NHCH(CH$_2$CH(CH$_3$)$_2$))—C(OH)(SO$_3$M)-H, PhCH$_2$SO$_2$-VA-NHCH(CH$_2$CH(CH$_3$)$_2$))—C(OH)(SO$_3$M)-H, PhCH$_2$O(OH)(O)P-LA-NHCH(CH$_2$CH(CH$_3$)$_2$))—C(OH)(SO$_3$M)-H, PhCH$_2$O(OH)(O)P-FA-NHCH(CH$_2$CH(CH$_3$)$_2$))—C(OH)(SO$_3$M)-H, and MeO(OH)(O)P-LGA- NHCH($CH_2$CH($CH_3$)$_2$))—C(OH)($SO_3$M)-H, wherein Ac is acetyl and Cbz is benzyloxycarbonyl.

16. A peptide aldehyde hydrosulfite adduct compound having the formula X—$B^1$—NH—CHR—CHOH—$SO_3$M; wherein R is a group such that NH—CHR—CO is an L or D-amino acid residue and M is H (hydrogen) or an alkali metal; $B^1$ represents one amino acid residue which is different from proline (Pro); X is $B^2$, $B^3$—$B^2$, Z—$B^2$, Z—$B^3$—$B^2$, wherein $B^3$ and $B^2$ each represents one amino acid residue, and Z is an N-terminal protection group; and wherein $B^2$ is Gly, Thr or Val.

17. A peptide aldehyde hydrosulfite adduct compound having the formula X—$B^1$—NH—CHR—CHOH—SO3M; wherein R is a group such that NH—CHR—CO is an L or D-amino acid residue and M is H (hydrogen) or an alkali metal; $B^1$ represents one amino acid residue which is different from proline (Pro); X is $B^3$—$B^2$, Z—$B^3$—$B^2$, wherein $B^3$ and $B^2$ each represents one amino acid residue, and Z is an N-terminal protection group; and wherein $B^3$ is Phe, Tyr, Trp, Phenylglycine, Leu, Val, Nva, Nle or Ile.

18. A composition comprising a subtilisin and a peptide aldehyde hydrosulfite adduct compound of claim 12.

19. A composition comprising a subtilisin and a peptide aldehyde hydrosulfite adduct compound of claim 14.

20. A composition comprising a subtilisin and a peptide aldehyde hydrosulfite adduct compound of claim 16.

21. A composition comprising a subtilisin and a peptide aldehyde hydrosulfite adduct compound of claim 17.

* * * * *